(12) United States Patent
Burghardt et al.

(10) Patent No.: US 9,994,507 B2
(45) Date of Patent: Jun. 12, 2018

(54) OPTIMIZED METHOD FOR PRODUCING METHACROLEIN

(71) Applicant: EVONIK RÖHM GMBH, Darmstadt (DE)

(72) Inventors: Rudolf Burghardt, Darmstadt (DE); Steffen Krill, Mühltal (DE); Torsten Balduf, Pfungstadt (DE); Gerhard Koelbl, Gernsheim (DE); Martin Koestner, Darmstadt (DE); Eduard Rundal, Frankfurt (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days. days.

(21) Appl. No.: 15/511,108

(22) PCT Filed: Sep. 16, 2015

(86) PCT No.: PCT/EP2015/071146
§ 371 (c)(1),
(2) Date: Mar. 14, 2017

(87) PCT Pub. No.: WO2016/042000
PCT Pub. Date: Mar. 24, 2016

(65) Prior Publication Data
US 2017/0275227 A1    Sep. 28, 2017

(30) Foreign Application Priority Data

Sep. 18, 2014    (EP) .................................... 14185345

(51) Int. Cl.
*C07C 45/75* (2006.01)
*C07C 69/00* (2006.01)
*C07C 67/44* (2006.01)

(52) U.S. Cl.
CPC ............ *C07C 45/75* (2013.01); *Y02P 20/582* (2015.11)

(58) Field of Classification Search
CPC ........ C07C 45/75; C07C 69/732; C07C 67/44
USPC ......................................................... 568/458
See application file for complete search history.

(56) References Cited

U.S. PATENT DOCUMENTS 4,496,770 A    1/1985    Duembgen et al.
9,580,374 B2   2/2017    Krill et al.

FOREIGN PATENT DOCUMENTS

DE            32 13 681 A1    10/1983

OTHER PUBLICATIONS

International Search Report dated Nov. 30, 2015 in PCT/EP2015/071146 filed Sep. 16, 2015.
European Search Report dated Mar. 13, 2015 in European Application 14185345.7 filed Sep. 18, 2014.
U.S. Appl. No. 14/773,602, filed Sep. 8, 2015, US 2016-0031786 A1, Torsten Balduf et al.
U.S. Appl. No. 14/784,320, filed Oct. 14, 2015, US 2016-0068464 A1, Steffen Krill et al.
U.S. Appl. No. 14/904,898, filed Jan. 13, 2016, US 2016-0138804 A1, Steffen Krill et al.
U.S. Appl. No. 15/030,775, filed Apr. 20, 2016, US 2016-0251301 A1, Steffen Krill et al.
U.S. Appl. No. 15/037,212, filed May 17, 2016, US 2016-0280628 A1, Steffen Krill et al.

*Primary Examiner* — Sikarl A Witherspoon
(74) *Attorney, Agent, or Firm* — Oblon, McClelland, Maier & Neustadt, L.L.P.

(57) ABSTRACT

The present invention relates to an optimized process for the preparation of methacrolein. Methacrolein is used in chemical synthesis particularly as an intermediate for the preparation of methacrylic acid, methyl methacrylate or even active ingredients, fragrances or flavorings. In particular the present invention relates to the optimization of the process parameters by which, inter alia, a reduction of the content of harmful dimeric methacrolein in the end product may be achieved.

14 Claims, No Drawings

OPTIMIZED METHOD FOR PRODUCING METHACROLEIN

The present invention relates to an optimized process for the preparation of methacrolein. Methacrolein is used in chemical synthesis particularly as an intermediate for the preparation of methacrylic acid, methyl methacrylate or even active ingredients, fragrances or flavourings. In particular the present invention relates to the optimization of the process parameters by which, inter alia, a reduction of the content of harmful dimeric methacrolein in the end product may be achieved.

There exists a great interest in very simple, economically viable and environmentally friendly preparation processes for methacrolein.

PRIOR ART

In the preparation of methacrolein by the so-called $C_2$ process, the target product is obtained from formalin and propionaldehyde in the presence of a secondary amine and an acid, usually an organic acid. In this case, the reaction is effected via a Mannich reaction. The methacrolein (MAL) synthesized in this way can then be converted in a subsequent step to methacrylic acid by oxidation in the gas phase or to methyl methacrylate by oxidative esterification. Such a process for the preparation of methacrolein is described, inter alia, in the publications U.S. Pat. No. 7,141,702, U.S. Pat. No. 4,408,079, JP 3069420, JP 4173757, EP 0 317 909 and U.S. Pat. No. 2,848,499.

The processes based on a Mannich reaction suitable for the preparation of methacrolein are generally known to those skilled in the art and are the subject of corresponding review articles, for example in Ullmann's Encyclopedia of Industrial Chemistry 2012, Wiley-VCH Verlag GmbH & Co. KGaA, Weinheim, Acrolein and Methacrolein, DOI: 10.1002/14356007.a01_149.pub2.

For economic utilization of this process, a high yield and a low specific energy requirement should be attained. According to the teaching of EP 0 194 620, a low content of dimeric methacrolein (DIMAL) in the product, preferably less than 0.2% by weight, and a propionaldehyde content of less than 1% by weight should be sought, in order to avoid lasting damage to the oxidation catalyst of the optional subsequent heterogeneous gas phase catalysis.

A process for the preparation of MAL is described in DE 3213681 which is particularly characterized in that the reaction is carried out at a temperature of greater than 150° C. with a reaction time of at most 25 min in the presence of secondary amines and optionally of acids. In the best case, propionaldehyde is reacted with formalin at temperatures of 162 to 205° C. and a residence time of 6 seconds. The yield in the best case is 97.2% and the DIMAL content is low, but almost 1% by weight. The water content in the feed is 40% by weight and the amine concentration is 2.5% by weight based on the water content. The distinctly low yield and the comparatively high DIMAL content show that this method is less advantageous.

In a further embodiment of DE 3213681, the reactor is operated at an inlet temperature of 161° C. and the temperature increases up to 184° C. due to the strongly exothermic reaction. The residence time is ca. 6.9 sec. The water content in the feed to the reaction is ca. 50% by weight. The amine content based on the water is 1.8% by weight. For instance, a DIMAL content of 0.29% by weight is observed at a yield of 98.1% using such a process variant. According to the teaching of EP 0 194 620, this MAL is obviously not ideally suited to be used in a heterogeneous gas phase oxidation.

U.S. Pat. No. 4,408,079 describes a process for preparing MAL in which the reaction of propionaldehyde with formalin is carried out at a molar ratio of between 0.9 and 1.5 to 1, a pH between 2.5 and 7 and temperatures of 0° C. to 150° C. in the presence of a secondary amine at a concentration of 0.025 to 0.75 or of 0.05 to 1.5 mol, and organic acids at a concentration of 0.05 to 1.5 mol, based in each case on 1 mol of propionaldehyde. In comparison to the teaching of DE 3213681, the selected temperature range is therefore significantly lower. According to U.S. Pat. No. 4,408,079, the reaction is carried out here continuously in a stirred tank cascade of two to three reactors at very long residence times of the reactants of 10 to 90 min. With this embodiment of the method, relatively low yields of 91 to 96% are achieved. Performing the reaction at low temperatures therefore shows considerable disadvantages. In addition to a significantly reduced yield, the stirred tank reactors used are linked to high investment costs and are complicated to maintain compared to the reactor disclosed in DE 3213681. The DIMAL contents of the products are unknown. On downstream processing of the examples, despite the comparatively low temperatures, high contents of significantly more than 1% by weight of harmful dimeric methacrolein were formed. Such methacrolein of this quality is not economically viable in any subsequent stage without further processing.

Therefore, for a variety of reasons, there exists a great interest in providing a process for preparing MAL comprising lower amounts of DIMAL than is possible using the methods of the prior art. This plays a major role in the further processing of the MAL in the gas phase oxidation to methacrylic acid, particularly in relation to the effect as catalyst poison. Especially, however, for the oxidative esterification of the MAL to MMA is a low DIMAL content desirable, since DIMAL or conversion products thereof also have to be removed from the product in this process, which is costly and inconvenient, or they interfere with the reaction to a considerable degree. Furthermore, DIMAL contents in the work-up lead to colouring of the conversion products.

OBJECT

In view of the prior art it was therefore the object of the present invention to provide a process for preparing methacrolein by the $C_2$ process with which, firstly, high yields of methacrolein can be obtained and secondly the product can be introduced without further work-up processes into a gas phase oxidation to give methacrylic acid or in an oxidative esterification to give methyl methacrylate (MMA).

In particular, therefore, the object consisted of being able to prepare MAL using this process having a DIMAL content, without further work-up, of less than 0.5% by weight, preferably less than 0.2% by weight.

Further objects not mentioned explicitly will become apparent from the overall context of the following description and the claims.

SOLUTION

These objects are achieved by means of a novel process for continuously performing a Mannich reaction, by means of which methacrolein is prepared from formaldehyde and propionaldehyde using at least one acid and at least one organic base as catalysts. This reaction is carried out in this case according to the invention in a continuously operated tubular reactor or plate reactor—abbreviated to reactor below—using temperature gradients. The inlet temperature of the feeding of the reactants and catalysts into the reactor is in this case between 100 and less than 150° C., preferably between 110 and 140° C. and the temperature of the reaction mixture at the outflow of the reactor (outlet temperature) is at most 180° C., preferably between 150 and 180° C., particularly preferably between 155 and 170° C. The maximum temperature present overall in the reactor is especially preferably 170° C., particularly 165° C. Furthermore, the water content in the reactor feed is greater than 45% by weight and at most 85% by weight and the amount of organic base in the reactor feed is more than 5 mol %, based on 100 mol % propionaldehyde in the feed. In this context, the organic base comprises, in addition to the pure base, the respective base part in the salts with the acid and in the base-containing intermediates of the Mannich reaction.

The internal pressure of the reactor is also adjusted such that this is greater than the boiling pressure of the reaction mixture. In other words, pressure and temperature are adjusted such that the reaction is always carried out below the boiling point of the reaction mixture, thus the reaction proceeds in the liquid phase. The internal pressure in the reactor is preferably between 10 and 50 bar, particularly preferably between 20 and 50 bar.

In accordance with the invention, feeding of the reactants into the reactor is understood to mean the overall feed, composed of the fresh feed from the reactants required for the reaction and the optional recycling stream. The optional recycling streams can, for example, be wholly or partly fed back into the reactor from the work-up of the methacrolein-containing mixture which is removed from the reactor outlet or from a downstream distillation column as an aqueous solution from the bottom of the column. This is especially important in the further information below on the composition of the feed. A continuously operated reactor is often, even preferably, operated in the case of the Mannich reaction described under at least partial recycling of recycling streams. Under constant operation, this forms a stationary phase in the reactor which may vary from the composition of the fresh feed, particularly with respect to the catalyst components, such that in the reactor there is a higher catalyst concentration than that introduced in the fresh feed. The fresh feed mentioned is generally composed of a propionaldehyde stream, a formalin stream, a stream of the organic base and the acid stream. In this case, there may be different embodiments with respect to the supply line of these streams into the reactor. Firstly, it is possible that all or some of the components are already present as a mixture and are passed into the reactor together. As an alternative, it is also possible that all or part of the reactants not present as a mixture are passed directly into the reactor in individual streams. Furthermore, an embodiment is also possible in which all or some of the reactants are mixed with one another in a mixing chamber upstream of the reactor or are brought together in a common line prior to being passed into the reactor. However, it is important to ensure that, when all the components are mixed with one another at the inlet temperature, the residence time outside the reactor should be kept particularly short, since the reaction is started here and is therefore attributable to the actual residence time.

In said optional mixing chamber, the mixing of the monomers may be assisted by means of a static or dynamic mixer. The mixing may also be effected by means of an injection point designed for this purpose in the mixing chamber. Furthermore, it is possible to effect the mixing by means of such an injection point directly at the inlet of the reactor.

The reactants are generally used pure or as solutions, particularly as aqueous solutions. In particular, formaldehyde is generally used as formalin, i.e. as an aqueous solution, at a concentration between 35 and 60% by weight.

The residence time of the reaction mixture in the reactor should be kept rather short in spite of the lower inlet temperature compared with the prior art. In particular, the residence time in the reactor is between 1 and 30 s, preferably between 5 and 15 s and especially preferably between 7 and 12 s. At excessively short residence times, costs in terms of the overall yield result or an excessive inlet temperature in the reactor or excessive maximum temperature in the reactor is required to ensure a complete conversion of the reactants. It has also been observed, surprisingly, that the formation of dimeric MAL is also supressed with shorter residence times in the reactor. Thus, rather shorter residence times within the limits described are preferred for the reaction regime.

According to the invention, it is in particular a surprisingly effective change, relative to the prior art, that the starting materials are led into the reactor at a significantly lower temperature, while the residence time within the reactor surprisingly does not have to be relevantly extended. It has been found in this case, particularly surprisingly, that such a reaction regime leads to the formation of distinctly lower amounts of dimeric methacrolein.

With regard to the composition of the reaction mixture, compositions in the reactor feed particularly have a ratio of propionaldehyde to formaldehyde of between 0.75 to 1 mol and 1 to 1.2 mol, particularly preferably between 1 to 0.98 mol and 1 to 1.02 mol.

Equally preferred are compositions of the feed in which base is present at between 0.05 and 0.15 mol, preferably between 0.06 and 0.1 mol and particularly preferably between 0.06 and 0.08 mol, based on one mole of propionaldehyde. With preference, at least 20% of the total amount of organic base in the feed originate from the fresh feed and the remainder accordingly preferably originate from the recycling stream. Furthermore, a feed is preferred in which acid is present at between 0.8 and 1.5, preferably between 0.9 and 1.3 and particularly preferably between 1 and 1.2 mol, based on one mole of organic base. The ratio of the equivalents of amine to acid and the specific choice thereof is preferably selected such that, measured at 20° C. and standard pressure in the reaction mixture prior to the reaction, a pH of 3.0 to 7.0, preferably 3.5 to 6.5 results.

The acids are generally inorganic acids or organic mono-, di- or polycarboxylic acids, preferably monocarboxylic acids, particularly aliphatic monocarboxylic acids. For the reaction of propanal and formaldehyde, particular preference is given to using at least one organic acid, particularly preferably formic acid, acetic acid and/or propionic acid, especially preferably acetic acid.

The organic bases are preferably amines, particularly preferably secondary amines. Suitable amines are, for example: dimethylamine, diethylamine, methylethylamine, methylpropylamine, dipropylamine, dibutylamine, di-isopropylamine, di-isobutylamine, methylisopropylamine, methylisobutylamine, methyl-sec-butylamine, methyl(2-methylpentyl)amine, methyl(2-ethylhexyl)amine, pyrrolidine, piperidine, morpholine, N-methylpiperazine, N-hydroxyethylpiperazine, piperazine, hexamethyleneimine, diethanolamine, methylethanolamine, methylcyclohexylamine, methylcyclopentylamine, dicyclohexylamine or corresponding mixtures. A particularly preferred organic base is dimethylamine.

The water content of the feed from the fresh feed and recycling stream, as described according to the invention, is between 45 and 85% by weight. The water content of the feed is preferably between 50 and 70% by weight. Water contents in the feed between 55 and 65% by weight have proven to be particularly advantageous.

The tubular reactor used in accordance with the invention preferably has an internal diameter of an individual tube between 4 and 20 mm, particularly preferably between 8 and 15 mm. In particular, several tubular reactors in the form of a shell-and-tube reactor are used. As an alternative to the shell-and-tube reactor or single tubular reactors, the inventive process may also be carried out with less preference in a plate reactor with heat exchanger, in particular having a plate gap between 0.5 and 10 mm, preferably 1 to 5 mm. The plate reactor in this context may also be a fully welded plate heat exchanger with sufficient compressive strength.

It has proven to be particularly advantageous in this case, if the tubular reactors are perfused at a superficial flow velocity between 0.3 and 2.0 m/s, preferably 0.8 to 1.2 m/s, especially preferably between 0.85 and 0.90 m/s. The tubular reactors especially preferably have, in addition, optional static mixers.

It is especially advantageous if the reactor, starting from the feed, has at least one adiabatic zone, a subsequent cooling zone and a second adiabatic zone at the outlet. The cooling is effected in this case, particularly in the middle zone, wholly or partly with the aid of a cooling circuit. This cooling circuit may be variously configured and can be readily devised in the specific construction by those skilled in the art. Firstly, it is possible to introduce a preheated condensate into the cooling jacket and to conduct away again steam generated. It is also possible to lead a cooling liquid, particularly water or an oil stable at the operating temperatures, under pressure into the circuit such that the cooling liquid remains liquid even on heating. The internal temperature and gradient thereof are particularly set by a combination of the heat transfer coefficient, the chosen cooling temperature and the cooling method and by selecting the operating mode of the reactor with respect to a cooling jacket in cocurrent or in countercurrent. The cooling liquid is generally introduced into the cooling jacket at a temperature between 100 and 140° C.

Equally preferred is a methacrolein concentration of the reaction mixture at the outflow between 20 and 50% by weight.

In the preparation of methacrolein from propanol and formaldehyde, the reaction mixture reacted in the reactor is preferably passed from the discharge into a column and stripped therein with the steam formed from the water introduced. The product leaves the column overhead together with water. The mixture is condensed and separated by means of a phase separation vessel into an upper phase and a lower phase. The upper phase contains the methacrolein. The lower phase consists principally of water. This water can preferably be fed back again at least partly, preferably completely, into the column for removal of the product still dissolved therein. A part of the aqueous phase in the bottoms is removed continuously or in a batchwise manner in such a case and is passed to a work-up or disposal. This may be a membrane separation stage, a further distillation, a biological disposal—depending on the constituents present—or a thermal oxidizer.

It has proven to be particularly advantageous if at least 20% by weight, preferably at least 50% by weight and particularly preferably at least 60% by weight of the aqueous phase from the bottoms are recycled into the inlet of the tubular reactor. This percentage portion is referred to below as recycling rate. It has been shown, surprisingly, due to this measure and the additional dilution of the reaction solution linked thereto, at the same time at almost the same or increasing catalyst concentration, that even less dimeric methacrolein is formed by the method according to the invention and the selectivity of the reaction is even higher.

The reactor may additionally have further zones. In particular, an optional heat transfer zone can be mentioned, in which the reaction mixture is cooler than the cooling liquid of the reactor jacket. Such a zone may result in a relatively cool feed at a temperature of 100° C. or only slightly warmer, for example, directly behind the first adiabatic zone. Alternatively, the heat transfer zone may also be located as a preheating zone before the first adiabatic zone.

The exact recycling rate to be set arises from the desired water content in the reactor and the amounts of water which are introduced into the reactor via the reactants and catalyst components. This applies in particular to the formalin. However, it is also possible to feed in the organic base and/or the acid as aqueous solutions. In addition, the propionaldehyde may also have, for example, up to 5% by weight of water.

The water present in the reactor in the preparation of methacrolein from propanal and formaldehyde comes from the water which was added as catalyst solution, the water of reaction formed during the reaction and optionally together with the water present in the formaldehyde solution. However, further water sources to be considered to a lesser extent are constituents of the technical grade reactants such as propanal, and water that is formed in various side reactions of the catalyst components with reactants, by-products and reaction products, and water of reaction from all these components which form under the reaction conditions.

By-products of the reaction may arise in various ways. As examples which may be initially mentioned here are especially by-products of the catalyst components such as higher alkylated amines, particularly trimethylamine when using dimethylamine as original amine catalyst. Small amounts of reactants may also be present in the discharge. Examples of these are methacrolein, formaldehyde, paraformaldehyde and propanal. By-products of the reaction to be mentioned which are equally present in the amine-containing water of reaction, would be, for example, dimers, oligomers or polymers of methacrolein. Furthermore, depending on the process regime, other auxiliaries such as organic solvents, e.g. methanol, formic acid, propanol, dioxane, tetrahydrofuran or methoxyethanol may also be present—and also further substances formed or present in the reaction matrix.

A particularly surprising advantage of the present invention is that, in the reaction regime according to the invention, by-products that are especially difficult to remove and/or directly impair the yield are formed in significantly lower amounts than is known from methods of the prior art. Therefore, the process overall can be carried out with a high yield, without particularly complex purification steps being necessary.

It has been found, particularly surprisingly in this case, that the proportion of dimeric methacrolein formed by the reaction regime according to the invention is reduced compared to the methods of the prior art, and that the formation of oligomers or polymers of methacrolein is almost completely avoided.

This has not only a great significance in relation to the resulting increase in yield, which is based on the fact that the dimerization, oligomerization or polymerization of the product is avoided. In particular, the decrease of the dimeric methacrolein has a major significance with respect to potential subsequent reactions. For instance, methacrolein, as already illustrated in the embodiments of the prior art, is in particular further processed in an oxidation to methacrylic acid. For the catalysts used in these oxidation processes, dimeric methacrolein has, however, proven to be a catalyst poison. This in turn decreases either the lifetime of the catalysts or additional further purification steps between the two reaction stages must be carried out, which, inter alia, additionally reduce the yield.

Additional disadvantages also arise, however, for an alternative use of the methacrolein in an oxidative esterification, for example, to methyl methacrylate (MMA). For instance, an undesirable yellowing is observed in MMA thus prepared, particularly on storage. Such discolouration cannot be observed with methacrolein based on the inventive process or on MMA prepared based on another methacrolein having only a very low proportion of dimer.

Furthermore, it has been found, surprisingly, that significant energy savings can be achieved, in addition to higher purity and yield, particularly compared to processes of the prior art.

A major advantage of the present invention is also that the process can be carried out with relatively simple and inexpensive system components. The components are linked to low investment costs. Here, the systems are easy to maintain and offer low maintenance costs.

The methacrolein obtained may be purified after removal from the outlet of the tubular reactor. In particular, such a purification may be purified by means of at least one distillation and at least one phase separation subsequent usually to the first distillation as described. Subsequently, the purified methacrolein may be converted to methacrylic acid, particularly in a gas phase oxidation. Alternatively, and equally preferred, the purified methacrolein is converted to methyl methacrylate by oxidative esterification.

EXAMPLES

The process according to the invention and the resulting advantages are further described below with reference to these examples, although these are not to be interpreted as limiting the invention in any way.

Examples 1 to 9/Comparative Examples 1 to 11
(See Table 1)

A formalin solution having a formaldehyde content of 37% by weight or 55% by weight, depending on the example, and propionaldehyde are mixed by means of a static mixer (referred to below as aldehyde solution) and the mixture is subsequently heated to the desired temperature (see Table 1) in an oil-heated heat exchanger. The exact water content of the formalin, depending on the example, plays no further role, since this completely enters the water content of the fresh feed in accordance with Table 1. A recycle stream, which adjoins the tubular reactor from the bottom of the product column, is mixed with acetic acid and dimethylamine (as 40% solution in water) and is likewise pre-heated to the desired temperature. The pre-heated aldehyde solution and the pre-heated catalyst solution are mixed in a further static mixer. This starting mixture is then fed to a temperature-controlled, by means of oil, tubular reactor.

The reaction is typically carried out at pressures of ca. 35 to 40 bar. The product mixture at the outflow of the tubular reactor is released via a valve and enters the product column for the distillation. At the top of this column, after condensation and phase separation, a biphasic mixture of methacrolein and an aqueous phase is obtained. The aqueous phase is fed back to the column. The organic phase enters the product container. At the bottom of the column, a partial stream is fed back into the reaction as recycling. Another partial stream is removed as aqueous product into a further product container.

In examples 1 to 4, in accordance with the process according to the invention, methacrolein having a DIMAL content of less than 0.2% by weight is obtained. The water content is ca. 56% by weight and the dimethylamine content, based on the water in the feed, is ca. 2.7% by weight. The temperature in the reactor is between 122° C. as inlet temperature and 153° C. as outlet temperature. Significant temperature spikes do not occur.

Examples 5 to 7 are less preferred since here a dimeric MAL content below 0.4% by weight, but not below 0.2% by weight, could be achieved. The distinction with examples 1 to 4 here is especially the higher maximum temperature and outlet temperature in addition to, in part, a higher inlet temperature.

Examples 8 and 9 are still less preferred since here a dimeric MAL content below 0.5% by weight, but not below 0.4 or even 0.2% by weight, could be achieved. Here, the inlet temperatures and particularly the maximum temperatures were even higher. In particular, the maximum temperatures were above the preferred maximum temperature of 165° C. or even 170° C.

Although comparative example 1 leads to a product having 0.49% by weight, thus attaining a DIMAL content less than 0.5% by weight, which is the object of this invention, it does not meet the object of the invention due to a excessively low amine concentration. If these results are compared with those of the very similar example 8, which leads to the same DIMAL concentration in the product, the selectivity of the reaction and the conversion are worse. Furthermore, it is observed that the residence times are shorter and the temperatures lower in comparative example 1 than in the procedure of example 8. Therefore, a significantly lower DIMAL concentration should be expected. Since this is not the case however, it clearly follows from this that the amine concentration surprisingly plays a major role in the formation of by-product as well.

Comparative example 4 was carried out at a likewise too low amine concentration at relatively high temperatures and residence times, even if still within the respective limits according to the invention. Thus, the heat exposure of the reaction mixture was significantly higher compared with comparative example 1 and it even resulted in a DIMAL content of greater than 0.9% by weight.

Comparative examples 2 and 3 had relatively low DMA contents. In particular, these were carried out, however, at an inlet temperature considerably above 150° C. A DIMAL content of even significantly greater than 1.0% by weight accordingly resulted.

Comparative examples 4 and 7 were carried out with a too low content of organic base (DMA). Comparative examples 5 and 7 were carried out, in contrast or in addition, with a water content which was no longer in accordance with the invention at less than 50% by weight. All the examples led to products with comparable selectivities and conversions with at the same time very high DIMAL contents in the product of more than 0.6% by weight.

Comparative examples 8 and 9 were in turn not carried out in accordance with the invention having inlet temperatures above 150° C. and correspondingly very high maximum and outlet temperatures. The DIMAL contents were thus too high, despite the high inlet temperatures being countered with a very dilute procedure, short residence times and a relatively high amine concentration.

Comparative Example 10 (Batch Process)

Propionaldehyde and formaldehyde, in the form of formalin (in a molar ratio of 1:1) are initially charged in a 1 L autoclave. The autoclave, temperature-controlled by means of an oil bath, is sealed and pressurized with 40 bar nitrogen. The content is stirred and heated to ca. 120° C. On reaching the target temperature, the catalyst solution composed of water, dimethylamine and acetic acid (0.07 parts of dimethylamine to one part propionaldehyde, and an acid to base ratio of 1.1 to 1.0) is added. The water concentration in the feed was ca. 56% by weight and the water loading with dimethylamine was 2.5% by weight. After about 20 min, the experiment is terminated and the autoclave is cooled in a stirred ice bath. The mixture is removed and separated by means of phase separation into an organic and an aqueous phase. Both phases are investigated with respect to their composition. The propionaldehyde conversion is 99.8% by weight, the yield of MAL is 75.9% by weight and the DIMAL content of the methacrolein is 11.26% by weight.

Comparative Examples 11, 12 and 13 (Batch Experiments, See Table 2)

Propionaldehyde and formaldehyde, in the form of formalin (molar ratio of 1:1) are initially charged in a 0.45 L autoclave. The autoclave, temperature-controlled by means of an oil bath, is sealed and pressurized with 40 bar nitrogen. The content is stirred and heated to ca. 115° C. On reaching the target temperature, the catalyst solution of water, dimethylamine and acetic acid is added. After the desired time, the experiment is terminated and the autoclave is cooled in a stirred ice bath. The mixture is removed and separated by means of phase separation into an organic and an aqueous phase. Both phases are investigated with respect to their composition. The results are summarized in Table 2.

TABLE 2

Batch experiments (comparative examples 11 to 13)

| | PA:FO mol/mol | DMA:PA mol % | ACOH:DMA mol/mol | H2O % by wt. | DMA/H2O % by wt. | RT min | T OIL ° C. | X PA % by wt. | SMAL % by wt. | c DIMAL % by wt. |
|---|---|---|---|---|---|---|---|---|---|---|
| CE 11 | 1 | 0.065 | 1.10 | 68 | 1.4 | 34 | 115 | 99.4 | 86 | 4.8 |
| CE 12 | 1 | 0.075 | 1.10 | 68 | 1.5 | 16 | 115 | 98.8 | 90 | 2.9 |
| CE 13 | 1 | 0.075 | 1.10 | 68 | 1.5 | 2 | 115 | 98.3 | 87 | 1.7 |

According to the results presented in Table 2, performing the reaction at an overall temperature of 115° C. is not of interest, since the desired DIMAL concentration in the product is too high in all three comparative examples 11 to 13. Furthermore, in a batch process, poorer yields and/or too high concentrations of dimeric MAL result due to the longer residence time required.

The examples show in particular, in relation to the results of the comparative examples, that the combination of features of the first claim in particular lead to very good yields with a simultaneously low proportion of dimeric methacrolein in the product.

TABLE 1

| | PA:FO | DMA:PA | ACOH:DMA | Recycle | DMA:PA | H₂O | DMA/H2O | RT |
|---|---|---|---|---|---|---|---|---|
| | Fresh feed | | | | Reactor inlet | | | |
| | mol/mol | mol % | mol/mol | % | mol % | % | % | sec |
| DE3213681A1 Ex 1 | 1 | 3.7 | 1.08 | — | — | 50 | 1.8 | 6.9 |
| DE3213681A1 Ex 2 | 1 | 3.6 | 1.14 | — | — | 40 | 2.5 | 6 |
| Example 1 | 0.99 | 2.50 | 1.09 | 70.5 | 7.8 | 55.6 | 2.74 | 9.30 |
| Example 2 | 0.99 | 2.51 | 1.09 | 71.0 | 7.8 | 56.1 | 2.74 | 9.26 |
| Example 3 | 0.98 | 2.61 | 1.09 | 71.2 | 8.2 | 54.9 | 2.82 | 9.41 |
| Example 4 | 0.96 | 2.51 | 1.09 | 70.1 | 7.7 | 56.5 | 2.71 | 9.21 |
| Example 5 | 0.99 | 2.51 | 1.09 | 70.5 | 7.8 | 55.7 | 2.75 | 9.26 |
| Example 6 | 0.99 | 2.51 | 1.09 | 70.4 | 7.8 | 55.6 | 2.75 | 9.30 |
| Example 7 | 0.98 | 2.50 | 1.09 | 70.5 | 7.7 | 56.0 | 2.72 | 9.22 |
| Example 8 | 0.99 | 2.51 | 1.09 | 70.5 | 7.8 | 55.6 | 2.74 | 9.26 |
| Example 9 | 0.99 | 2.52 | 1.08 | 70.4 | 7.8 | 55.6 | 2.76 | 9.26 |
| CE 1 | 0.99 | 2.50 | 1.09 | 48.8 | 4.7 | 56.4 | 1.76 | 9.23 |
| CE 2 | 1.01 | 2.49 | 1.10 | 52.8 | 5.2 | 58.4 | 1.73 | 11.26 |
| CE 3 | 1.00 | 2.52 | 1.09 | 53.5 | 5.2 | 58.7 | 1.73 | 11.23 |
| CE 4 | 1.00 | 2.50 | 1.11 | 49.3 | 4.8 | 68.5 | 1.75 | 9.33 |
| CE 5 | 1.00 | 4.83 | 1.10 | 16.5 | 5.7 | 41.8 | 3.78 | 12.27 |

TABLE 1-continued

| | | | | | | | | |
|---|---|---|---|---|---|---|---|---|
| CE 6 | 0.99 | 4.81 | 1.09 | 16.7 | 5.7 | 42.3 | 3.73 | 12.21 |
| CE 7 | 0.99 | 4.01 | 1.10 | 16.6 | 4.8 | 41.7 | 3.11 | 12.32 |
| CE 8 | 1.00 | 2.50 | 1.10 | 65.3 | 6.7 | 83.9 | 1.66 | 7.66 |
| CE 9 | 1.01 | 2.50 | 1.10 | 65.0 | 6.5 | 64.8 | 1.63 | 7.68 |

| | $T_{oil}$ °C. | $T_{in}$ °C. | $T_{max}$ | $T_{out}$ °C. | Conversion of PA % | Selec. MAL % | c DIMAL % |
|---|---|---|---|---|---|---|---|
| DE3213681A1 Ex 1 | | 161 | 184 | — | 99.5 | 98.1 | 0.29 |
| DE3213681A1 Ex 2 | | 162 | 205 | — | >99.4 | 97.2 | <1 |
| Example 1 | 139.5 | 122.5 | 152.6 | 152.2 | 99.37 | 98.75 | 0.18 |
| Example 2 | 139.1 | 122.5 | 152.3 | 152.0 | 99.30 | 98.85 | 0.18 |
| Example 3 | 139.9 | 122.1 | 152.3 | 152.2 | 99.35 | 98.67 | 0.18 |
| Example 4 | 139.1 | 122.8 | 153.0 | 153.0 | 99.46 | 98.33 | 0.18 |
| Example 5 | 143.9 | 129.9 | 160.2 | 155.5 | 99.75 | 98.19 | 0.34 |
| Example 6 | 144.2 | 127.3 | 157.7 | 154.7 | 99.65 | 98.47 | 0.27 |
| Example 7 | 139.0 | 122.5 | 156.3 | 154.9 | 99.57 | 98.62 | 0.22 |
| Example 8 | 159.8 | 142.1 | 173.0 | 169.1 | 99.67 | 98.03 | 0.49 |
| Example 9 | 146.4 | 133.8 | 165.4 | 159.7 | 99.77 | 98.34 | 0.45 |
| CE 1 | 159.5 | 141.0 | 172.3 | 169.6 | 99.65 | 98.02 | 0.49 |
| CE 2 | 164.1 | 155.7 | 179.6 | 172.7 | 99.81 | 98.51 | 1.35 |
| CE 3 | 164.0 | 150.3 | 177.5 | 168.7 | 99.83 | 98.40 | 1.13 |
| CE 4 | 158.2 | 147.2 | 173.0 | 164.4 | 99.81 | 97.91 | 0.92 |
| CE 5 | 149.1 | 150.5 | 179.8 | 167.8 | 99.32 | 96.44 | 0.93 |
| CE 6 | 148.4 | 142.2 | 172.2 | 158.6 | 99.17 | 98.05 | 0.65 |
| CE 7 | 153.6 | 141.5 | 171.9 | 159.2 | 99.66 | 98.58 | 0.68 |
| CE 8 | 158.8 | 154.2 | 171.7 | 171.7 | 99.58 | 98.18 | 0.94 |
| CE 9 | 158.9 | 150.3 | 171.7 | 171.7 | 99.68 | 98.34 | 0.65 |

The invention claimed is:

1. A process for continuously performing a Mannich reaction, comprising:
   preparing methacrolein from formaldehyde and propionaldehyde as reactants using at least one acid and at least one organic base as catalysts,
   carrying out the reaction in a continuously operated tubular reactor or plate reactor using a temperature gradient, wherein an inlet temperature of a reactor feed of the reactants and the catalysts into the reactor is between 100 and less than 150° C. and the temperature of a reaction mixture at the outflow of the reactor is at most 180° C.,
   wherein a water content in the reactor feed is greater than 45% by weight and at most 85% by weight,
   wherein an amount of organic base in the reactor feed, comprising the pure base and also the respective base partly in a salt with the acid and in a base-containing intermediate of the Mannich reaction, is more than 5 mol % based on propionaldehyde,
   wherein an internal pressure of the reactor is adjusted such that this is greater than the boiling pressure of the reaction mixture, and
   wherein a residence time of the reaction mixture in the reactor is between 1 and 30 s.

2. The process according to claim 1, wherein the reactor feed has a ratio of propionaldehyde to formaldehyde between 0.75 to 1 mol and 1 to 0.8 mol.

3. The process according to claim 1, wherein at least 20% of the total amount of organic base in the reactor feed originates from fresh feed, and that the reactor feed comprises between 1 and 1.5 mol of acid based on one mole of organic base.

4. The process according to claim 3, wherein the organic base is a secondary amine and the acid is formic acid, acetic acid and/or propionic acid.

5. The process according to claim 1, wherein the maximum temperature in the reactor is at most 170° C.

6. The process according to claim 1, wherein the inlet temperature in the reactor is between 110 and 140° C., and the temperature of the reaction mixture in the outflow is between 155 and 170° C.

7. The process according to claim 1, wherein the reactor is a tubular reactor in the form of a shell-and-tube reactor with an individual tube having an internal diameter between 4 and 20 mm.

8. The process according to claim 1, wherein the tubular reactor is employed and is perfused at a superficial flow velocity between 0.3 and 2.0 m/s and optionally has a static mixer.

9. The process according to claim 1, wherein a methacrolein concentration of the reaction mixture at the outflow is between 20 and 50% by weight.

10. The process according to claim 1, wherein a reacted reaction solution after removal at an outlet of the reactor is distilled in a column and the methacrolein is subsequently separated in a phase separation vessel from a separated aqueous phase, wherein said separated aqueous phase is wholly or partly fed back into the column.

11. The process according to claim 10, wherein at least 20% by weight of an aqueous phase from the bottoms of the column are recycled into the inlet of the tubular reactor.

12. The process according to claim 1, wherein the residence time of the reaction mixture in the reactor is between 5 and 15 s.

13. The process according to claim 1, wherein the methacrolein is purified by at least one distillation and at least one phase separation and is subsequently converted to methacrylic acid in a gas phase oxidation.

14. The process according to claim 1, wherein the methacrolein is purified by at least one distillation and at least one phase separation and is subsequently converted to methyl methacrylate by oxidative esterification.

* * * * *